US00RE40045E

(19) United States
(12) Reissued Patent
Palmer

(10) Patent Number: US RE40,045 E
(45) **Date of Reissued Patent: *Feb. 5, 2008**

(54) MEDICAMENTS

(75) Inventor: James B. D. Palmer, Princeton, NJ (US)

(73) Assignee: Glaxo Group Limited, Greenford (GB)

( * ) Notice: This patent is subject to a terminal disclaimer.

(21) Appl. No.: 10/933,483

(22) Filed: Sep. 3, 2004

Related U.S. Patent Documents

Reissue of:
(64) Patent No.: 5,270,305
Issued: Dec. 14, 1993
Appl. No.: 07/753,907
Filed: Sep. 3, 1991

U.S. Applications:
(63) Continuation of application No. 07/578,601, filed on Sep. 7, 1990, now abandoned.

(30) Foreign Application Priority Data

Sep. 8, 1989 (GB) ..... 8920392
Oct. 20, 1989 (GB) ..... 8923644

(51) Int. Cl.
*A61K 9/00* (2006.01)
*A61K 9/14* (2006.01)
*A61L 9/04* (2006.01)

(52) U.S. Cl. ..... 424/43; 424/400; 424/434; 424/45; 424/46; 424/489; 514/826

(58) Field of Classification Search ..... 424/400, 424/422, 434, 450, 489, 43, 45, 46; 514/826, 514/951
See application file for complete search history.

(56) References Cited

U.S. PATENT DOCUMENTS 4,199,578 A 4/1980 Stevenson
4,278,673 A * 7/1981 Hartley et al. ..... 514/243
4,335,121 A * 6/1982 Phillipps et al. ..... 514/180
4,352,789 A 10/1982 Thiel
4,513,001 A * 4/1985 Joannic et al. ..... 514/394
4,578,221 A 3/1986 Phillipps et al.
4,778,054 A * 10/1988 Newell et al. ..... 206/531
4,811,731 A * 3/1989 Newell et al. ..... 128/203.15
4,814,161 A * 3/1989 Jinks et al. ..... 424/45
4,866,051 A * 9/1989 Hunt et al. ..... 514/180
4,906,476 A * 3/1990 Radhakrishnan ..... 424/450
4,985,418 A * 1/1991 Richards ..... 514/179
5,091,422 A 2/1992 Skidmore et al.
5,208,226 A 5/1993 Palmer
5,658,549 A * 8/1997 Akehurst et al. ..... 424/45
5,674,472 A * 10/1997 Akehurst et al. ..... 424/45
5,736,124 A * 4/1998 Akehurst et al. ..... 424/45
5,817,293 A * 10/1998 Akehurst et al. ..... 424/45
5,916,540 A * 6/1999 Akehurst et al. ..... 424/45
5,955,439 A * 9/1999 Green ..... 514/23
6,143,277 A * 11/2000 Ashurst et al. ..... 424/45
6,153,173 A * 11/2000 Sapsford et al. ..... 424/45
6,251,368 B1 * 6/2001 Akehurst et al. ..... 424/45
6,253,762 B1 * 7/2001 Britto ..... 128/200.14
6,536,427 B2 * 3/2003 Davies et al. ..... 128/203.15
6,880,722 B2 * 4/2005 Anderson et al. ..... 221/71
6,919,069 B2 * 7/2005 Akehurst et al. ..... 424/45
6,926,178 B1 * 8/2005 Anderson ..... 222/402.2

FOREIGN PATENT DOCUMENTS

EP 0 223 671 A1 5/1987
EP 0 416 951 A1 3/1991
GB 2 088 877 A 6/1982
GB 2 107 715 A 5/1983
GB 2107715 * 5/1983
GB 2140800 A 12/1984
GB 2140800 * 12/1984
GB 2187953 * 9/1987
GB 2 187 953 A 9/1987
GB 2 235 626 A 3/1991
GB 2 235 627 A 3/1991
WO WO87/05213 * 9/1987
WO WO 87/05213 A1 9/1987
WO WO-90/06775 A1 6/1990

OTHER PUBLICATIONS

Mikhail et al, Is twice daily prophylaxis with salbutamol and beclomethasone dipropionate effective in the management of asthma, Pharmatherapeutica, vol. 4 (10), 1986.*
Harding et al, A Comparison of the Tolerance and Systemic Effects of Fluticasone Propionate (FP) and Beclomethasone Dipropionate (BDP) in Healthy Volunteers, European Respiratory Journal, 1 (2): 196S, 1988.*
Ullman et al, Salmeterol, a new long acting inhaled beta–2–adrenoceptor agonist: comparison with sulbutamol in adult asthmatic patients, Thorax, 1988, 43:674–678.*
Barazzone, C., Asthme: nouveautés thérapeutiques (Asthma: new therapies), Médecine et Hygiene, 48:3642–3645 (1990).
Holtkamp, U., Glucocorticoide früher einsetzen (Apply Glucocorticoids Earlier), Deutsche Apotheker Zeitung (German Pharmacists Journal), 130(8):407–408 (1990).
Bronchodilators, in New Yakurigaku ("New Pharmacology"), Ed. by Chikako Tanaka and Ryuichi Katoh, Nankoudou, K.K., 427–428 (1989).
ABPI data sheet compendium entry for 1988–9 ("the VENTIDE data sheet").
Allergy and asthma, new trends and approaches to therapy. (Proceedings of a November 1987 conference) Ed. by A.B. Kay, Blackwell Scientific Publications, Boston, MA (1989).
Bauer, K. et al., The Effect of Inhaled Fluticasone Propionate (FP), A New Potent Corticosteriod in Severe Asthma, European Respiratory Journal, 1 (Suppl. 2): 201S (1988) (Abstract).
Bradshaw, J. et al., The Design of Salmeterol, a Long–acting Selective $\beta_2$–adrenoceptor agonist, Brit. Pharm. Soc'y, Oxford, England, UK, Sep. 9–11, 1987. Br. J. Pharmacology 92 Suppl. (1987) (Abstract 590P).

(Continued)

*Primary Examiner*—Sharmila Gollamudi
(74) *Attorney, Agent, or Firm*—Covington & Burling LLP

(57) ABSTRACT

Pharmaceutical compositions comprising effective amounts of salmeterol (and a physiologically acceptable salt thereof) and fluctuations propionate as a combined preparation for simultaneous, sequential or separate administration by inhalation in the treatment of respiratory disorders.

7 Claims, No Drawings

OTHER PUBLICATIONS

Brittain et al, Further Studies on the long duration of action of salmeterol, a new, selective Beta$_2$–stimulant bronchodilator, 125th Brit. Pharm. Conference, Aberdeen, Scotland, UK, Sep. 11–17, 1988, J. Pharm. Pharmacology 40 Suppl. (1988) (Abstract 93P).

Cochrane, G.M. et al., A Colour Atlas of Asthma (1989).

Cochrane, G.M., The Difficult Chronic Asthmatic, Br. J. Dis. Chest, 81(4): 313–320 (1987).

Crane, J. et al., Prescribed Fenoterol and Death from Asthma in New Zealand, 1981–83: Case–Control Study, The Lancet, 917–922 (1989).

Dal Negro, R.W. et al., Chronic Airways Obstruction Responsiveness to Combined, Pressurized Salbutamol–Beclomethasone Dipropionate (Ventolin Flogo*), Clinical Trials Journal, 20(6):366–372 (1983).

Drazen, J.M. et al., Comparison of Regularly Scheduled with As–Needed Use of Albuterol in Mild Asthma, The New England Journal of Medicine, 335(12):841–847 (1996).

Entzian, P. et al., Glucocorticoid receptor binding is influenced by a beta adrenoceptor agonist in vitro, Department of Medicine, Christian–Albrechts–Universitat, Kiel, FRG European Respiratory Journal, 1 (Suppl. 2): 196S (1988) (Abstract).

Fancourt, G.J. et al., The effects of high does (2000 micrograms/day) inhaled Beclomethasone dipropionate (Becloforte) on glucose tolerance in diet controlled elderly diabetic subjects, Leicester General Hospital Leicester, England European Respiratory Journal, 1 (Suppl. 2): 196S (1988) (Abstract).

Galleguillos, F., Study on the Association of Beclomethasone Dipropionate (BDP) and Salbutamol Ventide® In the Treatment of Asthma, Annals of Allergy (55 2 of Pt. 2) 407:Abstract 726 (1985).

Glaxo's R&D progressing on target, SCRIP No. 1411 (May 12, 1989).

Davies, Saffron, Health: Breathing space is not the same as a cure for asthmatics: Saffron Davies on the fears that new drugs to cope with the symptoms of asthma neglect to treat the disease itself, The Independent (Apr. 18, 1989).

Harding, S.M. et al., A Comparison of the Tolerance and Systemic Effects of Fluticasone Propionate (FP) and Beclomethasone Dipropionate (BDP) in Healthy Volunteers, European Respiratory Journal, 1 (Suppl. 2): 196S (1988) (Abstract).

Jeppsson, A.B. et al., Pharmacodynamic and pharmacokinetic aspects on the transport of bronchodilator drugs through the tracheal epithelium of the guinea pig, Pharmacol. Toxicol. (Copenhagen), 64(1):58–63 (Chemical Abstracts 110:147583r) (1989).

Kerrebijn, K.F. et al., Effect of long–term treatment with inhaled corticosteroids and beta–agonists on the bronchial responsiveness in children with asthma, J. Allergy Clin. Immunol., 79(4):653–659 (1987).

Kotaniemi, J. et al., Salbutamol Controlled Release Tablets (Volmax)® and Individually Titrated Slow Release Theophylline (Theo–Dur)® in the management of Chronic Obstructive Airways Disease (COAD), Central Hospitals, Sweden European Respiratory Journal, 1 (Suppl. 2): 196S (1988) (Abstract).

Kraan, J. et al., Changes in bronchial hyperreactivity induced by 4 weeks of treatment with antiasthmatic drugs in patients with allergic ashtma: A comparison between budesonide and terbutaline, J. Allergy Clin. Immunol., 76(4):628–636 (1985).

Lindsay, Fixed does combination therapy in the treatment of asthma—the case against it, Mechanism in Asthma: Pharmacology, Physiology and Management, pp. 421–425 (1988).

McDonald, C. et al., Evaluation of the combination inhaler of salbutamol and beclomethasone dipropionate in the management of asthma, Current Medical Research and Opinion, 11(2):116–122 (1988).

Mikhail, J.R. et al., is twice daily prophylaxis with salbutamol and beclomethasone dipropionate effective in the management of asthma?, Pharmatherapeutica, 4(10):648–654 (1986).

Martindale The Extra Pharmacopoeia, 882–883 (James E. F. Reynolds et al. eds., The Pharmaceutical Press, 29th ed. 1989).

Mitchell, E.A., Is current treatment increasing asthma mortality and morbity?, 44 Thorax 81–84 (1989).

Muers, M. et al., Effect of a timed interval between inhalation of beta–agonist and corticosteroid aersols on the control of chronic asthma, Thorax, 38:378–382 (1983).

Page, C.P., Developments in Asthma: A view of current research (PJB Publications Ltd. 1987).

Page, C.P., One explanation of the asthma paradox: inhibition of natural anti–inflammatory mechanism by $\beta_2$–agonists, The Lancet, 37:717–720 (1991).

Perri, G. et al., Salbutamol plus beclomethasone dipropionate (Ventolin Flogo) vs. fenoterol (Dosberotec) in chronic obstructive lung disease therapeutic strategy: a 4–week clinical trial, International Journal of Clinical Pharmacology, Therapy and Toxicology, 23(5):274–278 (1985).

Sears, M.R. et al., Regular inhaled beta–agonist treatment in bronical asthma, The Lancet, 336:1391–96 (1990).

Twentyman, O.P. et al., Controversies in respiratory medicine: regular inhaled β–agonists—clear clinical benefit or a hazar to health? (1) β–agonists can be used safely and beneficially in asthma, Respiratory Medicine, 86:471–476 (1992).

Ventolin compositum, Unlisted Drugs 33(6):101c (1981).

Vathenen, A.S. et al., Rebound Increase in Bronchial Responsiveness after Treatment with Inhaled Terbutaline, The Lancet, 554–557 (1988).

Woolcock, A.J., Aerosol Bronchodilators in Preventive Treatment of Asthma, Drugs 15:1–2 (1978).

Anani, A. et al., Breath–actuated inhalers: comparison of terbutaline Turbohaler with salbutamol Rotahaler, European Respiratory Journal, 2:640–642 (1989).

Arossa, W. et al., Salbutamol plus beclomethasone dipropionate versus theophylline for the prevention of methacholine–induced bronchospasm in patients with chronic bronchitis, International Journal of Clinical Pharmacology, Therapy and Toxicology, 23(10):565–568 (1985).

Ball, D.I. et al., Bronchodilator Activity of Salmeterol, A Long–acting $\beta_2$–Adrenoceptor Agonist, British Journal of Pharmacology, 92:746P (1987).

Ball, D.I. et al., In Vitro Characterisation of the $\beta_2$–Adrenoceptor agonist, Salmeterol, British Journal of Pharmacology, vol. 92:591P (1987).

Barnes, P.J., The Drug Therapy of Asthma: Directions for the 21st Century, Directions for New Anti–Asthma Drugs, 293–313 (Stella R. O'Donnell et al. eds. 1988).

Bateman, E.D. et al., Salmeterol/Fluticasone Combination Inhaler, A New, Effective and Well Tolerated Treatment for Asthma, Clin. Drug. Invest., 16(3):193–201 (1998).

Bennati, D. et al., Changes in Bronchial Reactivity in Asthmatic Children After Treatment with Beclomethasone Alone or in Association with Salbutamol, Journal of Asthma, 26(6):359–364 (1989).

Bloomfield, P. et al., Comparison of salbutamol given intravenously and by intermittent positive–pressure breathing in life–threatening asthma, British Medical Journal, 1(6167):848–850 (1979).

British Thoracic Society, Guidelines for management of asthma in adults: I—Chronic persistent asthma, British Medical Journal, 301: 651–653 (Sep. 29, 1990).

Butchers, P.R. et al., Salmeterol: A potent and long–acting inhibitor of the release of inflammatory and spasmogenic mediators from human lung, British Journal of Pharmacology, 92:745P (1987).

Carmichael, J. et al., Beclomethasone dipropionate dry–powder inhalation compared with conventional aerosol in chronic asthma, British Medical Journal, 2(6137):657–658 (1978).

Carmichael, J. et al., Corticosteroid resistance in chronic asthma, British Medical Journal, 282(6274):1419–1422 (1981).

Cameron, S.J. et al., Substitution of Beclomethasone Aerosol for Oral Prednisolone in the Treatment of Chronic Asthma, British Medical Journal, 4(5886):205–207 (1973).

Chapman, K.R. et al., Salmeterol and fluticasone propionate (50/250 μg) administered via combination Diskus inhaler: As effective as when given via separate Diskus Inhalers, Can. Resp. J., 6(1):45–51 (1999).

Chung, K.F. et al., Drug Treatment of Asthma, Drugs of Today, 25(11):721–732 (1989).

Church, M.K. et al., Influence of Salbutamol and Sodium Cromoglycate on Mast Cell Mediator Release In Vivo, The Journal of Allergy and Clinical Immunology, 75(1–Part 2):195 (1985) (Abstract 361).

Clark, R.A. et al., Is 200 μg Beclomethasone Diproprionate (BDP) Twice Daily as Effective as 100 μg Given Four Times Each Day?, Scottish Medical Journal, 30:195 (1985).

Clark, T.J.H. et al., The effects of beclomethasone dipropionate aerosol given in high doses to patients with asthma, Postgraduate Medical Journal, 51(Suppl. 4):72–75 (1975).

Clarke, S.W. et al., Therapeutic aerosols 2—Drugs available by the inhaled route, Thorax, 39(1):1–7 (1984).

Cochrane, G.M., et al., Algorithms for treatment of asthma, A Colour Atlas of Asthma, 125–129 (1989).

Cochrane, G.M., Inhaled Steroids and their role in the treatment of asthma, Bronchus, 2(3):8 (1987).

Combined inhaler is key to therapy, General Practitioner (Feb. 2, 1990).

Cooke, N.J. et al., Response to Rimiterol and Salbutamol Aerosols Administered by Intermittent Positive–pressure Ventilation, British Medical Journal, 2(5913):250–252 (1974).

Grant, I.W.B. et al., Becloforte inhaler, and further letter from Slessor, I.M. in British Medical Journal, 286(6365):645 (1983).

Costello, J.F. et al., Nebulised salbutamol in life–threatening asthma, and further letters of Anderson, P.B. and Bloomfield, P. et al., British Medical Journal, 1(6173):1284–1285 (1979).

Costello, J.F. et al., Response of patients receiving high dose beclomethasone dipropionate, Thorax, 7(29):571–573 (1974).

Creemers, J.P.H.M. et al., A Multicentre Comparative Study of Salbutamol Controlled Release (Volmax)® and Sustained–Release Theophylline (Theo–dur)® in the Control of Nocturnal Asthma, The European Respiratory Journal Abstracts Book, 1(Supplement 2):333s (1988).

Crompton, G., Intravenous β–agonist in severe acute asthma, British Medical Journal, and further letters of Ward, M.J. and McKay, S. et al., 297(6651):791–792 (1988).

Crompton, G.K., "All asthmatics should have inhaler therapy," The Pharmaceutical Journal, 232(6270):365–366 (1984).

Crompton, G.K., High dose inhaled steroids, Research and Clinical Forums, 11:51 (1989).

Crompton, G.K., Illogical warnings on Ventolin inhalers, Br. Med. J (Clin Res. Ed), 288(6425):1231 (1984).

Dal Negro, R.W. et al., Airways Flow Limitation: Acute Responsiveness to Combined Salbutamol+Beclomethasone Dipropionate (Ventolin® Flogo), Current Therapeutic Research, 35(4):561–565 (1984).

Deucher, N., Salmeterol—new 'designer' bronchodilator, Pulse, 14:86 (1989).

Douglas, J.G. et al., A Comparative Study of Two Doses of Salbutamol Nebulized at 4 and 8 Litres per Minute in Patients with Chronic Asthma, British Journal of Diseases of the Chest, 80(1):55–58 (1986).

Douglas, J.G. et al., Nebulised salbutamol without oxygen in severe acute asthma: how effective and how safe?, Thorax, 40(3):180–183 (1985).

Duncan, D. et al., Comparison of the Bronchodilator Effects of Salbutamol Inhaled as a Dry Powder and by Conventional Pressurised Aerosol, British Journal of Clinical Pharmacology, 4(6):669–671 (1977).

Duncan, D. et al., Salbutamol in the treatment of asthma, The Practitioner, 223:843–844 (1979).

Expert calls for dual drugs in asthma, General Practitioner, 19 (Mar. 17, 1989).

Extract from British National Formulary No. 16, "Drugs used in the treatment of diseases of the respiratory system," Chapter 3, 113–123 (1988).

Extracts from MIMS (1989) and MIMS (1990).

Nolte, D., Glucocorticoide in der Asthmatherapie, Deutsche Medizinische Wochenschrift, 114:1411–1415 (1989), together with English translation appended thereto "Glucocorticoids in the treatment of asthma".

Ferguson, A.C., Persistence of Bronchial Hyper–Responsiveness in Asthmatic Children Treated with Inhaled Beclomethasone, Supplement to Clinical and Investigative Medicine, 12(4):B5 (1989) (Abstract R–4).

Fergusson, R.J. et al., Nebulized Salbutamol in Life–Threatening Asthma: Is IPPB Necessary?, British Journal of Diseases of the Chest, 77(3):255–261 (1983).

Fischbacher, C.M. et al., Comparison of Duovent and Salbutamol Inhalers in Chronic Stable Asthma, Scottish Medical Journal, 30:195 (1985).

Flatt, A. et al., Comparison of Cardiovascular Effects of Inhaled Fenoterol, Salbutamol and Placebo, The European Respiratory Journal Abstracts Book, 1(Supplement 2):333s (1988).

Gader, A.M.A. et al., Fibrinoltic, Factor VIII and Pulse Rate Responses to Intravenous Adreline During Chronic Oral Salbutamol Administration, Thrombosis Research, 3(2):137–143 (1973).

Grant, I.W.B. et al., Beclomethasone Aerosol in Chronic Bronchial Asthma, with further letter of Turner–Warwick, M. et al., The Lancet, II(7884):838–839 (1974).

Gregg, I., A new treatment for asthma: promotional expediency versus pharmaceutical responsibility, with further letter of Slessor, I.M., British Medical Journal, 288(6410):68–69 (1984).

Gregg, I., Treatment of Asthma with Beclomethasone Aerosol, with further letter of Grant, I.W.B. et al., British Medical Journal, 2(5805):110 (1972).

Haahtela, T. et al., The superiority of combination beclomethasone and salbutamol over standard dosing of salbutamol in the treatment of chronic asthma, Annals of Allergy, 62(1):63–66 (1989).

Howarth, P.H. et al., Influence of Salbutamol and Sodium Cromoglycate on Mast Cell Mediator Release in vivo, Respiration, 46(S1):22–23 (1984) (Abstract).

Ind, P.W., Rational treatment of asthma, British Medical Journal, 288(6415):484–485 (1984).

Jack, D., The Challenge of Drug Discovery, Drug Design and Delivery, 4(3):167–186 (J.S. Morley et al. eds., Harwood Academic Publishers 1989).

Jeppsson, A.–B. et al., Pharmacodynamic and Pharmacokinetic Aspects on the Transport of Bronchodilator Drugs Through the Tracheal Epithelium of the Guinea–Pig, Pharmacology & Toxicology, 64(1):58–63 (1989).

Joubert, J.R. et al., Inhalation therapy during acute asthma, South African Medical Journal, 68(6):381–384 (1985).

Kemp, J.P. et al., A Comparative Study of Salmeterol, Albuterol, and Placebo via MDI in Asthmatic Adults, The Journal of Allergy and Clinical Immunology, 83(1):186 (1989) (Abstract 58).

Konig, P., The role of inhaled steroids in the treatment of asthma, Respiratory Medicine, 83(Supplement A):43–47 (1989).

Leitch, A.G. et al., Effect of intravenous infusion of salbutamol on ventilatory response to carbon dioxide and hypoxia and on heart rate and plasma potassium in normal men, British Medical Journal, 1(6006):365–367 (1976).

Lipworth, B. et al., The Pharmacokinetics of Salbutamol Controlled Release Tablets (SCR) in Asthmatic Patients, The European Respiratory Journal Abstracts Book, 1(Supplement 2):333s (1988).

Lipworth, B.J. et al., Airways, tremor and haemodynamic responses to inhaled salbutamol in normal subjects, British Journal of Clinical Pharmacology, 26(2):208P–209P (1988).

Lipworth, B.J. et al., Assessment of airways, tremor and chronotropic responses to inhaled salbutamol in the quantification of 2–adrenoceptor blockade, British Journal of Clinical Pharmacology, 28(1):95–102 (1989).

Lipworth, B.J. et al., β–adrenoceptor responses to high doses of inhaled salbutamol in patients with bronchial asthma, British Journal of Clinical Pharmacology, 26(5):527–533 (1988).

Lipworth, B.J. et al., β–Adrenoceptor Responses to High Doses of Inhaled Salbutamol in Asthma, Scottish Medical Journal, 33(1):219 (1988).

Lipworth, B.J. et al., β–Adrenoceptor Responses to Inhaled Salbutamol in Normal Subjects, European Journal of Clinical Pharmacology, 36(3):239–245 (1989).

Lipworth, B.J. et al., β–adrenoceptor responses to high doses of inhaled salbutamol aerosol in asthma, British Journal of Clinical Pharmacology, 25(5):625P (1988).

Lipworth, B.J. et al., β–adrenoceptor responses to inhaled salbutamol in the elderly, British Journal of Clinical Pharmacology, 28(6):725–729 (1989).

Lipworth, B.J. et al., $\beta_2$–adrenoceptor responses to salbutamol are unaltered in the elderly, British Journal of Clinical Pharmacology, 29(1):137P (1990).

Lipworth, B.J. et al., The biochemical effects of cumulative doses of inhaled salbutamol in normal subjects, British Journal of Clinical Pharmacology, 26(5):626P (1988).

Lipworth, B.J. et al., The biochemical effects of high–dose inhaled salbutamol in patients with asthma, European Journal of Clinical Pharmacology, 36(4):357–360 (1989).

Lipworth, B.J. et al., ECG and systemic responses to inhaled salbutamol are due to pulmonary rather than gut absorption, British Journal of Clinical Pharmacology, 27(5):662P (1989).

Lipworth, B.J. et al., Efficacy and systemic effects of salbutamol controlled release in asthma, British Journal of Clinical Pharmacology, 29(1):151P (1990).

Lipworth, B.J. et al., Evaluation of the metabolic responses to inhaled salbutamol in the measurement of $\beta_2$–adrenoceptor blockade, European Journal of Clinical Pharmacology, 37(3):297–300 (1989).

Lipworth, B.J. et al., Extrapulmonary effects of high dose inhaled salbutamol in normal and asthmatic subjects, The European Respiratory Journal Abstracts Book, 1(Supplement 2):199s (1988).

Lipworth, B.J. et al., Metabolic effects of cumulative doses of salbutamol from a metered–dose inhaler in bronchial asthma, British Journal of Clinical Pharmacology, 25(5):667P–668P (1988).

Lipworth, B.J. et al., Pharmacokinetics, efficacy and adverse effects of sublingual salbutamol in Patients with asthma, European Journal of Clinical Pharmacology, 37(6):567–571 (1989).

Lipworth, B.J. et al., Prior Treatment with Diuretic Augments the Hypokalaemic and Electrocardiographic Effects of Inhaled Salbutamol, Scottish Medical Journal, 34(4):508 (1989).

Lipworth, B.J. et al., Single dose and steady–state pharmacokinetics of 4 mg and 8 mg oral salbutamol controlled–release in patients with bronchial asthma, European Journal of Clinical Pharmacology, 36(Supplement):49–52 (1989).

Lipworth, B.J. et al., Systemic β–adrenoceptor responses to salbutamol given by metered–dose inhaler alone and with pear shaped spacer attachment: comparison of electrocardiographic, hypokalaemic and haemodynamic effects, British Journal of Clinical Pharmacology, 27(6):837–842 (1989).

Lipworth, B.J. et al., Tachphylaxis to Systemic But Not to Airway Responses during Prolonged Therapy with High Dose Inhaled Salbutamol in Asthmatics, American Review of Respiratory Disease, 140(3):586–592 (1989).

Löfdahl, C.G., Broaxaterol: Pharmacodynamic studies in patients with reversible airway obstruction, The European Respiratory Journal Abstracts Book, 1(Supplement 2): 199s (1988).
Maconochie, J.G. et al., An initial comparison of salmeterol and salbutamol against histamine–induced bronchoconstriction in healthy subjects, British Journal of Clinical Pharmacology, 25(1):115P (1988).
Maesen, F.P.V. et al., Evaluation of a new combination inhaler, Ventide, Journal for Drugtherapy and Research, 9(2):100–104 (1984).
Marsac, J.H. et al., Inhaled beta adrenergic agonists and inhaled steroids in the treatment of asthma, Allergy Immunology, Annals of Allergy, 63:220–224 (1989).
McAlpine, L.G. et al., Formoterol Protects Against Exercise–Induced Bronchospasm for Longer than Salbutamol, Scottish Medical Jornal, 34(4):508 (1989).
Meltzer, E.O. et al., A Dose Ranging Study of Fluticasone Propionate Aqueous Intranasal Spray (FP) in Patients with Seasonal Allergic Rhinitis (SAR), Journal of Allergy and Clinical Immunology, 83(1):279 (1989) (Abstract 428).
Mikhail, J., Is twice daily prophylaxis with salbutamol and beclomethasone dipropionate effective in the management of asthma?, European Journal of Respiratory Diseases, Supplement No. 146(69): A108 (1986).
Milne, L.J.R. et al., Beclomethasone Dipropionate and Oropharyngeal Candidiasis, British Medical Journal, 3(5934):797–798 (1974).
Milne, L.J.R. et al., Oropharyngeal thrush and beclomethasone dipropionate (Abstract), Postgraduate Medical Journal, 51(Supplement 4):53 (1975).
Morice, A.H. et al., A comparison of the effect of aminophylline and salbutamol on minute ventilation and the ventilatory response to carbon–dioxide, The Journal of British Thoracic Society, 40(3):234 (1985).
Morice, A.H. et al., A comparison of the ventilatory, cardiovascular and metabolic effects of salbutamol, aminophylline and vasoactive intestinal peptide in normal subjects, British Journal of Clinical Pharmacology, 22(2):149–153 (1986).
Neville, A. et al., Metabolic effects of salbutamol: comparison of aerosol and intravenous administration, British Medical Journal, 1(6058):413–414 (1977).
Nials, A.T. et al., The Interaction Between Salmeterol and β–Adrenoceptor Blocking Drugs on Guinea–Pig Isolated Trachea, British Journal of Pharmacology, 95:540P (1988).
Page, C.P. et al., Pathophysiology and pharmacology of asthma in "Side effects of anti–inflammatory drugs" Part 2. 331–344 (MIT Press 1987).
Palmer, J.B.D., β–Agonists in Asthma—Current Status and Future Developments, New Drugs for Asthma 12–20 (Peter J. Barnes ed., National Heart and Lung Institute 1989).
Paterson, I.C. et al., Further Studies of Rimiterol and Salbutamol Administered by Intermittent Positive–Pressure Ventilation, and an Important Observation on The Technique of Using the Bennett Ventilator, British Journal of Clinical Pharmacology, 4(5):605–609 (1977).
Pedersen, B. et al., A comparison of a new osmotic pressure mediated oral formulation of Salbutamol Controlled Release Tablets (Volmax®); SCR) and Standard Salbutamol Tablets (SST) in the treatment of mild asthma in adults, The European Respiratory Journal Abstracts Book, 1(Supplement 2):333s (1988).
The Pharmaceutical Journal, Ventolin and Becotide all in one, 454 (1983).
Plit, M. et al., Assessment of a new combination inhaler containing salbutamol and beclomethasone dipropionate in the management of asthmatic patients, South African Medical Journal, 65(19):758–762.
Pomari, C. et al., Multiparametrical approach to fog–challenge–induced bronchial hyperreactivity in asthmatics—protective effects of salbutamol plus beclomethasone dipropionate, International Journal of Clinical Pharmacology, Therapy and Toxicology, 22(9):515–518 (1984).
Pover, G.M. et al., Comparison of the Effects of Sequential or Simultaneous Administration of Salbutamol and Beclomethasone Dipropionate, Respiration, 50: 83–87 (1986).
Rafferty, P. et al., Budesonide and Beclomethasone Dipropionate in Severe Chronic Asthma Assessment of Prednisolone Sparing Properties, Scottish Medical Journal, 30:195 (1985).
Rafferty, P. et al., Comparison of Budesonide and Beclomethasone Dipropionate in Patients with Severe Chronic Asthma: Assessment of Relative Prednisolone–Sparing Effects, British Journal of Diseases of the Chest, 79(3):244–250 (1985).
Research Committee of the British Thoraic Association, Inhaled Beclomethasone Dipropionate in Allergic Bronchopulmonary Aspergillosis, British Journal of Diseases of the Chest, 73(4):349–356 (1979).
Rogers, A., Counseling on inhaler therapy, The Pharmaceutical Journal, 239(6455):652–3 (1987).
Ruffin, Richard E., Fixed dose combination therapy in asthma. The positive case for future therapy, Mechanisms in Asthma: Pharmacology, Physiology, and Management, 427–435 (1988).
Shenfield, G.M., Combination Bronchodilator Therapy, Drugs, 24(5):414–439 (1982).
Shenfield, G.M., Fixed Combination Drug Therapy, Drugs, 23(6):462–480 (1982).
Shepherd, G.L. et al., Regular versus symptomatic aerosol bronchodilator treatment of asthma, Br. J. Dis. Chest, 75:216 (1981).
Slessor, I.M., Addiction to aerosol treatment, British Medical Journal, 288(6145): 485 (1984).
Small, P. et al., The Effects of Intranasal Fluticasone Propionate on Allergen Induced Nasal Provocation, Supplement to Clinical and Investigative Medicine, 12(4):B5 (1989) (Abstract R–3).
Svedmyr, N., The current place of $\beta_2$ agonists in the management of asthma, The Proceedings of the Satellite Symposium of the 8th Congress of the European Society of Pneumology, Freiburg, Sep. 12, 1989 (Royal Society of Medicine Services Ltd 1990).
Turco, P. et al., Airways Flow Limitation: Responsiveness to Combined Salbutamol–Beclomethasone Dipropionate Proved with a New Simple Parameter, Current Therapeutic Research, 34(4):768–775 (1983).
Ullman, A. et al., A Dose–response Comparison of Inhaled Aerosol and Dry Powder Formulations of Salmeterol in Asthmatic Patients, American Review of Respiratory Disease, 137(6):435 (1988).
Ullman, A. et al., Inhaled Salmeterol—A New $\beta_2$–Adrenoceptor Agonist Produces Sustained Bronchodilation in Asthmatic Patients Without Causing Tachyphylaxis, American Review of Respiratory Disease, 137(6): page unavailable (1988).

Ullman, A. et al., Salmeterol, a new long acting inhaled $\beta_2$ adrenoceptor agonist: comparison with salbutamol in adult asthmatic patients, Thorax, 43(9):674–678 (1988).
van As, A. et al., A Dose–Tolerance Study of Intranasal Fluticasone Propionate Aqueous Nasal Spray in the Treatment of Seasonal Allergic Rhinitis, The Journal of Allergy and Clinical Immunology, 83(1):301 (1989) (Abstract 517).
Ventolin Rotacaps and Rotahaler Advertisement, Respiratory Disease, 140(2) (1989).
Ventide—A Useful Combination?, Drug and Therapeutics Bulletin, 24(4):15–16 (1986).
Waldeck, B. et al., New Possibilities for the β–Adrenoceptor Agonist Bronchodilator Drugs, Directions for New Anti–Asthma Drugs 55–68 (Stella R. O'Donnell et al. eds. 1988).
Willey, R.F. et al., Beclomethasone Dipropionate Aerosol and Oropharyngeal Candidiasis, British Journal of Diseases of the Chest, 70:32–38 (1976).
Willey, R.F. et al., Comparison of Twice Daily Administration of a New Cortcosteroid Budesonide with Beclomethasone Dipropionate Four Times Daily in the Treatment of Chronic Asthma, British Journal of Diseases of the Chest, 76(1):61–68 (1982).
Zenati, A. et al., Impiego clinico della associazione Salbutamolo–Beclometasone dipropionato in soggetti con bronchite cronica asmatiforme, IL Policlinico sezione medica, 91(3):473–478 (1984) (with English language abstract at the end of the article).
Abbott, A., New Directions in Asthma: Some Cause for Concern, Trends in Pharmacological Sciences, 9(5): 149–150 (1988).
American Academy of Pediatrics, Section on Allergy and Immunology, Management of Asthma, Pediatrics, 68(6):874–79 (1981).
Appel, D., Effect of Aminophylline When Added to Metaproterenol Sulfate and Beclomethasone Dipropionate Aerosol, Journal of Allergy and Clinical Immunology, 73(2):291–97 (1984).
Amaud, A. et al., Interaction Between Corticosteroids and Beta2–agonists in Acute Asthma, Eur. J. Resp. Dis. 63(Supp. 122):126–31 (1982).
Arnup, M. et al., Effects of Cold Air Hyperpnea in Patients with Chronic Obstructive Lung Disease, American Review of Respiratory Disease, 128(2):236–39 (1983).
Barnes, P., Asthma Therapy: Basic Mechanisms, Eur. J. Respir. Dis. Supplement, 217–65 (1986).
Barnes, P. et al., β–Adrenoceptors in Asthma and their Response to Agonists, Asthma: Physiology, Immunopharmacology & Treatment, 339, 350–351, 356 (Academic Press, London 1984).
Barnes, P., The Changing Face of Asthma, Quarterly Journal of Medicine, New Series, 63(241):359–65 (1987).
Barnes, P., Difficult Asthma, Cause for Concern, BMJ, 299:695–698 (Sep. 16, 1989).
Barnes, P., Effect of Corticosteroids on Airway Hyperresponsiveness, Am. Rev. Respir. Dis., 141:570–7 (1990).
Barnes, P., A New Approach to the Treatment of Asthma, The New England Journal of Medicine, 321(22):1517–27 (1989).
Barnes, P., New Concepts in the Pathogensis of Bronchial Hyperresponsiveness and Asthma, Allergy Clin. Immunol., 83(6):1013–27 (Jun. 1989).
Barnes, P. Nocturnal Asthma, The Practitioner, 231:479–81 (Apr. 8, 1987).
Barouni, I., et al., Comparisons of Therapy of Asthmatic Patients Treated with or Without Glucocorticoids: A Retrospektive Study, Eur. Resp. J. 1, supp. 2, 397S (1988) (abstract).
Basran, G. et al., Evidence in Man of Synergistic Interaction Between Putative Mediators of Acute Inflammation and Asthma, The Lancet, 935–37 (1982).
Beach, J., et al., A Comparison of the Effects of Salmeterol and Salbutamol on Rate of Recovery from Methacholine Challenge, European Respiratory Journal 3 (supp. 10), 113s–114s, 272 (Sep. 10, 1990).
Beasley R., et al., A Self Management Plan in the Treatment of Adult Asthma, Thorax (England), 44(3): 200–04 (Mar. 1989).
Beets, J., Actions of Locally Administered Adrenoreceptor Agonists on Increased Plasma Protein Extravasation and Blood Flow in Guinea–Pig Skin, Br. J. Pharmac., 70:461–467 (1980).
Bennati, D., et al., Changes in Bronchial Reactivity in Asthmatic Children After Treatment with Beclomethasone Alone or in Association with Salbutamol, Journal of Asthma (U.S.) 26(6): 359–64 (1989).
Berenbaum, M., Synergy, Additivism and Antagonism in Immunosuppression, Clin. Exp. Immunol., 28:1–18 (1977).
Bierman, W. et al., Dose–Response Study of Salmeterol, A Long Acting Beta2 Agonist, Thorax, 44(10):850P (1989) (abstract).
Boyd, G., et al., Placebo Controlled Comparison of the Bronchodilator Performance of Salmeterol and Salbutamol Over 12 Hours, Thorax 45(4): 340P (1990) (abstract).
Brittain, R., Approaches to a Long–Acting Selective Beta2–Adrenoceptor Stimulant, European Respiratory Journal 2 (supp. 8): 676s (abst. No. 200) (1989) (abstract).
British National Formulary, Drugs used in the treatment of diseases of the Respiratory System, Bronchodilators, Chapter 3.1, 116–128 (Mar. 1989).
Britton, M., Salmeterol: Three Month Comparison with Salbutamol in Asthmatic Patients, European Respiratory Journal 3 (supp. 10), 226s, S797 (1990) (abstract).
Browne, A. Science Report: Treatments May Lead to Increase in Asthma, The Times (London) Mar. 30, 1987 (news article).
Campos–Gongora, H., et al., Single Dose Comparison of Inhaled Salmeterol and Salbutamol on Airway Reactivity in Asthmatic Patients, European Respiratory Journal 3 (supp. 10), 114s, 273 (1990) (abstract).
Charpin, D., et al., Deep–Inspiration Induced Bronchoconstriction: A Mechanism for Beclomethasone Aerosol Intolerance, European Journal of Respiratory Diseases (Denmark), 64(7): 494–97 (Oct. 1983).
Chapman, B., Comparison of Terbutaline Via the Nebuhaler and Salbutamol Via the Volumatic: Theory and Practice, European Respiratory Journal, 3(5): 584–5 (1990).
Chung, K. et al., Respiratory and Allergic Disease, I., British Medical Journal, 296:29–33 (1988).
Chung, K. et al., Respiratory and Allergic Disease, II. Chronic Obstructive Airways Disease and Respiratory Infections, British Medical Journal, 296:111–15 (1988).
Church, M. et al., Inhibition of IgE–dependent Histamine Release from Human Dispersed Lung Mast Cells by Anti–Allergic Drugs and Salbutamol, Bri. J. Pharmac., 90:421–29 (1987).

Clark, T. (guest editor) et al., Bronchodilator Therapy: The Basis of Asthma and Chronic Obstructive Airways Disease Management, ADIS Press Limited, Auckland, New Zealand, 1–230 (1984).
Clark, R., Combined Therapy with Salbutamol and Beclomethasone Inhalers in Chronic Asthma, Lancet (England), 2(8080): 70–72 (Jul. 8, 1978).
Cluzel, M., et al., Ambulatory Long–Term Subcutaneous Salbutamol Infusion in Chronic Severe Asthma, Journal of Allergy and Clinical Immunology (U.S.), 85(3): 599–606 (Mar. 1990).
Cochrane, G., Bronchial Asthma and the Role of $\beta_2$–Agonists, Formoterol—a new generation β agonist, 24–30 (Barnes and Matthys eds., 1990).
Cockcroft, D., et al., Comparative Effects of Inhaled Salbutamol, Sodium Cromoglycate, and Beclomethasone Dipropionate on Allergen–Induced Early Asthmatic Responses, Late Asthmatic Responses, and Increased Bronchial Responsiveness to Histamine, Journal of Allergy and Clinical Immunology 79(5): 734–40 (May 1987).
Coleman, R., et al., Potency and Duration of Action of Salmeterol on Guinea–Pig Airways in Vitro and in Vivo, European Respiratory Journal 2 (supp. 8): 754s (1989) (abst. No. 558) (abstract).
Crane, J., Single–Dose Comparison of Salbutamol and Duovent–Berodual in Asthma, Respiration; International Review of Thoracic Diseases (Switzerland), 50 (supp. 2): 285–89 (1986).
Crompton, G. et al., Inhalation Therapy in the Management of Airway Obstruction, European Journal of Respiratory Diseases, 63 (Supp. 119):1–25 (1982).
Crompton, G.K., The Adult Patient's Difficulties with Inhalers, Lung, 168(Supp.):658–62 (1990).
Crompton, G.K., Nebulized or intravenous beta2 adrenoceptor agonist therapy in acute asthma?, The European Respiratory Journal, 3(2): 125–26 (1990).
Curzon, P., et al., Effect of Oral Prednisolone on Response to Salbutamol and Ipratropium Bromide Aerosols in Patients with Chronic Airflow Obstruction, Thorax (England), 38(8): 601–04 (Aug. 1983).
Dahl, R. et al., Nocturnal asthma: Effect of treatment with oral sustained–release terbutaline, inhaled budesonide, and the two in combination, Journal of Allergy and Clinical Immunology (United States), 83(4):811–5 (1989).
Dahl, R. et al., Effect on Lung Function of Budesonide by Inhalation, Terbutaline s.c. and Placebo Given Simultaneously or as Single Treatments, Eur. J. Respir. Dis. Suppl. 122:132–37 (1982).
Dahl, R., Salmeterol One Month Studies in Asthmatic Patients, European Respiratory Journal 2 (supp.8):677s (1989) (abstr. No. 203) (abstract).
Dahl, R., et al., The Influence of Inhaled Salmeterol on Bronchial Inflammation. A Bronchoalveolar Lavage Study in Patients with Bronchial Asthma, European Respiratory Journal 3 (supp. 10), 321s, 1279 (1990) (abstract).
Deuchar, N., New Drugs to Replace Oral Bronchodilators?, Pulse, Sep. 30, 1989, (news article).
Edmunds, A., et al., A Clinical Comparison of Beclomethasone Dipropionate Delivered by Pressurised Aerosol and as a Powder from a Rotahaler, Archives of Disease in Childhood (England), 54(3): 233–35 (Mar. 1979).
Fabbri, L, Effect of Antiasthma Drugs on Asthmatic Reactions Induced by Toluene Diisocynate in Sensitized Subjects, Lung (U.S.) 168 (supp.): 128–31 (1990).
Fawcett, I., et al., The Effect of Sodium Cromoglycate, Beclomethasone Dipropionate and Salbutamol on the Ventilatory Response to Cotton Dust in Mill Workers, British Journal of Diseases of the Chest (England), 72(1): 29–38 (Jan. 1978).
Fuller, R., et al., Anti–inflammatory Effects of Salmeterol, European Respiratory Journal 3 (supp. 10), 226s, S796 (1990) (abstract).
Glaxo's bronchodilator, salmeterol, SCRIP No. 1243, 23 (Sep. 25, 1987).
Glaxo's interim results "better than expected," SCRIP 1395, 10 (Mar. 17, 1989).
Glaxo's £1,000 million for new research facilities, SCRIP No. 1301, 8–9 (Apr. 20, 1988).
Glaxo Reports Research and Development Progress, PR Newswire (May 4, 1989).
Glaxo reveals its R&D portfolio, Pharmaceutical Business News (May 12, 1989).
Glaxo Reveals R&D, SCRIP No. 1184, 8–10 (Mar. 4, 1987).
Glaxo's Volmax introduced in UK, SCRIP No. 1274 (Jan. 15, 1988).
Grandordy, B. et al., Effect of betamethasone on airway obstruction and bronchial response to salbutamol in prednisolone resistant asthma, Thorax (England), 42(1):65–71 (1987).
Hambleton, G. et al., Is the Combination Inhaler of Salbutamol and Beclomethasone Dipropionate as Effective as the Same Agents from Separate Inhalers in the Management of Childhood Asthma,? Current Medical Research and Opinion, 10(8):548–54 (1987).
Harrison, A. et al., Interaction of Inhaled Corticosteroids and $Beta_2$–agonists in Asthmatic Subjects, Proceedings of the British Thoracic Society, 39:710–11 (1984) (abstract).
Harrison, R. et al., Hydrocortisone and Bronchial Beta–adrenergic Responsiveness, Proceedings of the Thoracic Society and the British Thoracic Association, 35:238 (1980) (abstract).
Henriksen, J. et al., Effects of Inhaled Budesonide Alone and in Combination with Low–Dose Terbutaline in Children with Exercise–Induced Asthma, American Review of Respiratory Disease, 128(6):993–997 (1983).
Hodgkinson, N., Asthma Drugs Could Kill, Say Specialists, The Times (London) Oct. 12, 1986 (news article).
Horn, C. et al., Compliance with Inhaled Therapy and Morbidity from Asthma, Respiratory Medicine, 84:67–70 (1990).
Interest in Glaxo's R&D, SCRIP No. 1177, 8 (Feb. 6, 1987).
Johnson, M., et al., Salmeterol: A Potent and Long–Acting B2–Adrenoceptor Agonist, European Respiratory Journal 2 (supp. 8): 676s (abst. No. 201) (1989) (abstract).
Johnson, M., The Pharmacology of Salmeterol, from A New Perspective in Asthma Therapy: Salmeterol, Satellite Symposium of the 8th Congress of the European Society of Pneumology, 10–24 (1989).
Kay, A. et al., "Pharmacological modulation of the asthmatic response", Current Perspectives in the Immunology of Respiratory Diseases, 30, 34 (A. B. Kay and Edward J. Goetzl eds., 1985).
Kreisman, H. et al., Dose–Response to Inhaled Salbutamol in the Emergency Treatment of Asthma, European Respiratory Journal 3 (supp. 10), 114s, 276 (1990) (abstract).

Lampa, E., Antitracheobronchospastic Interaction in Vitro and in Vivo Between Salbutamol and Flunisolide, Drugs under Experimental and Clinical Research, Bioscience Ediprint, Inc. XI(9):653–58 (1985).

Mackay, A. et al., How Important Is the Sequence of Administration of Inhaled Beclomethasone Dipropionate and Salbutamol in Asthma, British Journal of Diseases of the Chest (England), 75(3): 273–6 (1981).

Malo, J.L., et al., Formoterol, A New Inhaled Beta2–Adrenergic Agonist, Has A Longer Blocking Effect Than Salbutamol on Hyperventilation Induced Bronchoconstriction, European Respiratory Journal 3 (supp. 10), 113s, 271 (1990) (abstract).

Matera, C. et al., In Vivo and in Vitro Antitracheobronchospastic Interaction Between Salbutamol and Flunisolide and Possible Pharmacokinetic Interference, Rend. Atti. Accad. Aci. Med. Chir. 1986, 10:225–98 (Ital). (citation within Chemical Abstracts 108: 87603u: 20 (1988)) (abstract).

New approaches aimed at reducing deaths from asthma, Medical Times (Aug. 5–11, 1989).

New combined inhaler for chronic asthmatics, GP 71 (Oct. 21, 1983).

New Drug May Replace Inhaled Salbutamol, General Practitioner (Oct. 6, 1989).

New Drugs in Asthma and Allergy—Glaxo's salmeterol, SCRIP No. 1261, 22 (Nov. 27, 1987).

Nihon Glaxo's research plans, SCRIP No. 1425, 6 (Jun. 30, 1989).

Nippon Glaxo doubles capital, SCRIP No. 1391, 14 (Mar. 3, 1989).

Orgel, H. et al., Inhaled Albuterol Powder for the Treatment of Asthma—a Dose–Response Study, Journal of Allergy and Clinical Immunology 75: 468–471 (1985).

Palmer, J., Inhaled Salmeterol—Single Dose Studies, European Respiratory Journal 2 (supp. 8): 6765 (1989) (abst. No. 202) (1989) (abstract).

Partridge, M., Current Asthma Treatment (Chairman's commentary) and Current Problems in Asthma, extract from pamphlet from Symposium in Whitechapel, London (Nov. 25, 1988).

Pearson, R., Asthma: Management in Primary Care, Radcliff Medical Press Ltd, Oxford, Great Britain, 89, 95 (1990).

Pharmacotherapy in Bronchial Asthma; Opinions and recommendations from the group, Swedish Guidelines, 149–157 (pre 1990).

Poch, G., Clinical Trials with Combinations of Drugs, Prog. Clin. Pharma., 6:53–61 (1984).

Prentice, T., Deaths from Asthma Can Be Reduced, The Times (London) Jan. 19, 1988 (news article).

Prentice, T., Fight against Asthma: Inadequate Treatment is Blamed for Most Deaths from Disease, The Times (London) Aug. 11, 1986 (news article).

Price, A. et al., Salbutamol in the 1980s. A Reappraisal of its Clinical Efficacy, Drugs (United States), 38(1):77–122 (1989).

Salbutamol's Successor?, Pharmaceutical Journal 244: 414 (1990).

Salmeron, S. et al., High Doses of Inhaled Corticosteroids in Unstable, Chronic Asthma: A Multicenter, Double–blind, Placebo–controlled Study, American Review of Respiratory Diseases, 140:167–171 (1989).

Sandstrom, T. et al., Salmeterol—A New Long Acting Inhaled Beta–2–Agonist, in a Twelve Hours Dose–Effect Study, Allergy and Asthma Proc. (New England and Regional), 9(4): 378 Abstract No. 517 (1988) (abstract).

Sandstrom, T. et al., Salmeterol—A Dose Response Study with a Long Acting Inhaled $\beta_2$–Agonist, American Review of Respiratory Disease, 139(4):Annual Meeting Supplement Abstracts (Apr. 1989) (abstract).

Serevent® Inhaler, Product License No. 0045/0157, pp. 38–39, Allen & Hanbury's Limited (1989–1990).

Smith, M. et al., Effects of Long Term Inhaled High Dose Beclomethasone Dispropionate on Adrenal Function, Thorax, 38:676–81 (1983).

Souhami, R., et al., Textbook of Medicine, Churchill Livingstone, Edinburgh London Melbourne and New York (1990) (pp. 485–491).

Specialist Slams Failure to Curb Rising Asthma Toll, Doctor, Clinical (Oct. 13, 1988) (news article).

Suganuma, T. et al., The Effectiveness of Repetitive Administration of Fenoterol Metered Dose Inhalation (MDI) with Beclomethasone Dipropionate Inhalation (BDI), Allergy and Asthma Proc. (New England and Regional), 9(4):378 (1988) No. 520 (abstract).

Svedmyr, N. et al., Physiology and Pharmacodynamics of Beta–Adrenergic Agonists—Chapter 5, Drug Therapy for Asthma, 177–211 (1987).

Svedmyr, N., The Current Place of Beta2–Agonists in the Management of Asthma, European Respiratory Journal 2 (supp. 8): 676s (abst. No. 199) (1989) (abstract).

Tal, A. et al., Dexamethasone and Salbutamol in the Treatment of Acute Wheezing in Infants, Pediatrics (United States) 71(1):13–18 (1983).

Toomey, P., In Search of a Pattern and Cure for the Many Asthma Sufferers; The National Heart and Lung Institute, Focus, The Times (London) (Nov. 10, 1988) (news article).

Triptafen® and Triptafen®–M, Product License Nos. 0045/0128 and 0045/0129, p. 39, Allen & Hanbury's Limited (1989–1990).

Turner–Warwick, M., Epidemiology of Nocturnal Asthma, The American Journal of Medicine, 85(Suppl.1B):6–8 (1988).

Twentyman, O. et al., Protection against allergen–induced asthma by salmeterol, The Lancet, 336:1338–42 (1990).

UK Pharma companies' R&D assessed. SCRIP 1435 (Aug. 4, 1989).

Ventide® Inhaler, Produt License No. 0045/0122, p. 39, Allen & Hanbury's Limited (1989–1990).

Ventolin Inhaler, Product License No. 0045–5022R, Allen & Hanbury's Limited (Feb. 19, 1988).

Viskum, K., Inhaled Salmeterol Improves Control in Moderate to Severe Asthmatics: A 3 Month Study, European Respiratory Journal 3 (supp. 10), 235s, P839 (1990) (abstract).

Wilson, J. et al., Has the Change to Beta–Agonists Combined with Oral Theophylline Increased Cases of Fatal Asthma,? The Lancet, 1:1235–37 (1981).

Woolcock, A. et al., Asthma Management Plant, 1989, The Medical Journal of Australia, 151:650–53 (Dec. 18, 1989).

Ayrton, J. et al., Preclinical Development for Fluticasone Propionate, European Respiratory Journal, 3(Supp. 10) (1990) (Abstract No. S922).

Bierman, C. et al., A Dose–Response Study of Salmeterol, A Long Acting Beta2 Agonist, Allergologies 12:122 (1989) (Abstract No. FC 15.02).

Boyd, G. et al., A Placebo Controlled Comparison of the Bronchodilator Performance of Salmeterol and Salbutamol Over 12 Hours, British Thoraic Society Winter Meeting 1989, 56 (Abstract No. P141).
Brittain, R., Approaches to a Long–Acting Selective $\beta_2$–Adrenoceptor Stimulant, Lung, 168(Supp.):111–114 (1990).
Brogden, R. et al., Beclomethasone Dipropionate: A Reappraisal of Its Pharmacodynamic Properties and Therapeutic Efficacy After a Decade of Use in Asthma and Rhinitis, Drugs, 28(2):99–126 (1984).
Crane, J. et al., $\beta_2$–agonists in asthma, Letters to the Editor, The Lancet, 337:43 (1991).
Crompton, G.K., $\beta_2$–agonists in asthma, Letters to the Editor, The Lancet, 337:43–44 (1991).
Dahl, R., $\beta_2$–agonists in asthma, Letters to the Editor, The Lancet, 337:43 (1991).
Dahl, R. et al., The Influence of Inhaled Salmeterol on Bronchial Inflammation, A Bronchoalveolar Lavage Study in Patients with Bronchial Asthma, European Respiratory Journal, 3(Supp. 10):321s, 1280 (1990).
Davies, P. et al., A Comparative Trial of Two Slow–Release Theophylline Tablets in the Treatment of Asthma, Journal of International Medical Research (England), 12(4):261–65 (1984) (Abstract).
Deuchar, N., Salmeterol New 'Designer' Bronchodilator, Pulse, Oct. 14, 1989 at 86.
di Marzo, A., Glucocorticoids and Beta Agonists in the Treatment of Status Asthmaticus, Eur. J. Resp. Dis. 64(Supp. 126):564 (1984) (Abstract).
Diseases of the Upper Respiratory Tract, Respiratory Disease, 649–71.
Edwards, T. et al., The Salmeterol Xinafoate/Fluticasone Propionate Dry Powder Combination Products via Diskus Inhaler Improves Asthma Control Compared to Salmeterol Xinafoate or Fluticasone Propionate Dry Powder Alone, Abstract #105660, Allergy and Asthma Center of Albany Medical College, Albany, NY, Pharmaceutical Research, Dallas, TX: MS Asthma & Allergy Clinic, PA, Jackson, MS; New England Clinical Studies, Ltd., North Dartmouth, MA; Glaxo Wellcome Inc., Research Triangle Park, NC (article) (1998).
Ekelund, L., et al., Glucocorticoids and β–Adrenergic–Receptor Agonists: Their Combined Effect on Fetal Rabbit Lung Surfactant, Am. J. Obstet. Gynecol., 152(8):1063–66 (1985).
Fitzpatrick, M. et al., Efficacy of Salmeterol, a Long–Acting Inhaled $Beta_2$ Agonist in Nocturnal Asthma, American Review of Respiratory Disease, 141(4 pt.2):A209 (1990).
Fitzpatrick, M. et al., Inhaled Salmeterol Reduces Nocturnal Bronchocontriction and Improves Objective Sleep Quality in Nocturnal Asthma, Thorax, 45(1):789–790 (1990).
Fitzpatrick, M. et al., Salmeterol in Nocturnal Asthma: A Double Blind Placebo Controlled Trial of a Long Acting $Beta_2$ Agonist, British Medical Journal, 301(6765):1365–1368 (1990).
Frans, A. et al., Isolated Cough Which Responds to Inhaled Salbutamol and Beclomethasone Dipropionate, European Respiratory Journal (Denmark), 3(2):243 (1990) (Abstract).
Glaxo Salmeterol Twice–Daily Aerosol Bronchodilator, The Pink Sheet (USA). Issued by Corporate Communications (Jun. 11, 1990).
Grant, I.W.B. et al., Becloforte inhaler, British Medical Journal, 286:644–645 (1983).
Grassi, V. et al., Pneumologia, Medicina–Riv. E.M.I., 9:343–354 (1989).
Green, M., An Investigation into the Drug–Drug Interaction Between Corticosteroids and Beta Adrenergic Agonists, Pharmacology, (1979) 215 pp. available: Univ. Microfilms Int., Order No. 8008332 (From: Diss. Abstr. Int. B, 40(12, Pt. 1):5628 (1980).
Harding, S., The Human Pharmacology of Fluticasone Propionate, Respiratory Medicine, 84(Supp. A):25–29 (1990).
Harding, S. et al., The Clinical Pharmacology of Inhaled Fluticasone Propionate, European Respiratory Journal, 3(Supp. 10):250S, S923 (1990).
Higgs, C., The Effect of Regular Inhaled Salbutamol on the Airway Responsiveness of Normal Subjects, Clinical Science, 63(6):513–17 (1982).
Horn, C. et al., Can the Morbidity of Asthma be Reduced by High Dose Inhaled Therapy? A Prospective Study, Respiratory Medicine, 84(1):61–66 (1990).
Iafrate, R. et al., Current Concepts in Clinical Therapeutics: Asthma, Clinical Pharmacy, 5:206–27 (1986).
Ind, P., How I manage asthma in adults, Maternal and Child Health, 15:25–31 (1990).
Ind, P., Salmeterol, British Journal of Hospital Medicine, 44(5):343–344 (1990).
Jeppsson, A. et al., On the Predictive Value of Experiments in Vitro in the Evaluation of the Effect Duration of Bronchodilator Drugs for Local Administration, Pulmonary Pharmacology (Scotland), 2(2):81–85 (1989).
Johnson, M., The Pharmacology of Salmeterol, European Respiratory Journal, 2(Supp. 8):755S (1989) (Abst. No. 561a).
Johnson, M. et al., Salmeterol: A Potent and Long–Acting $\beta_2$–Adrenoceptor Agonist, European Respiratory Journal, 2(Supp. 8): 676s (1989) (Abst. No. 201).
Juniper, E. et al., Airway Responsiveness to Histamine and Methacholine: Relationship to Minimum Treatment to Control Symptoms of Asthma, Thorax, 36(8):575–79 (1981).
Juniper, E. et al., Long–Term Stability of Bronchial Responsiveness to Histamine, Thorax, 37(4):288–91 (1982) (Abstract).
Kemp, J. et al., A Comparative Study of Salmeterol, Albuterol, and Placebo via MDI in Asthmatic Adults, Journal of Allergy and Clinical Immunology, 83(1):186 (1989) (Abstract No. 58).
Kemp, J. et al., A One–Week Evaluation of Salmeterol, a New Long–Acting $Beta_2$–Adrenergic Aerosol, for Asthma Therapy, 258, J. Allergy Clin. Immunol. (1991) (Abstract No. 474).
Kraemer, R., Effects of Regular Inhalation of Beclomethasone Dipropionate and Sodium Cromoglycate on Bronchial Hyperreactivity in Asthmatic Children, Acta Paediatrica Scandinavica (Sweden), 76(1):119–23 (1987) (Abstract).
Kreus, K. et al., Treatment of Steroid–Dependent Asthma Patients with Beclomethasone Dipropionate Aerosol, Scandinavian Journal of Respiratory Diseases (Denmark), 56(1):47–57 (1975) (Abstract).
Lampa, E. et al., Antitracheobronchospastic Interaction in Vitro and in Vivo Between Salbutamol and Flunisolide, Drugs under Experimental and Clinical Research, Bioscience Ediprint, Inc., XI(9):653–58 (1985).
Lazarus, S., Rational Therapy of Acute Asthma, Annals of Allergy (U.S.), 63(6 Pt. 2):585–90 (1989) (Abstract).

Liley, H. et al., Glucocorticoids and Beta–Agonists Increase Expression of the Gene for Surfactant Protein of 28–36 kDa (SP–28–36), Clin. Res., 36(1):231A (1988).
Lipworth, B.J. et al., Comparison of the efficacy and systemic effects of 4 mg and 8 mg formulations of salbumatol controlled release in patients with asthma, European Journal of Clinical Pharmacology, 39(3):281–285 (1990).
Long–Acting Drug Set for Asthma Role, Doctor (Nov. 16, 1989) (news article).
Maayan, C. et al., The Functional Response of Infants with Persistent Wheezing to Nebulized Beclomethasone Dipropionate, Pediatric Pulmonology (U.S.), 2(1):9–14 (1986) (Abstract).
Maconochie, J. et al., The Effect of Treatment with Inhaled Salmeterol on the Response to Inhaled Salbutamol, European Respiratory Journal, 2(Supp. 8):841s (1989) (Abstract No. 921).
Marks, M., Prophylactic Drugs in the Management of Childhood Asthma, Annals of Allergy, 43(1):19–23 (1979) (Abstract).
Martindale The Extra Pharmacopoeia, "Salbutamol" and "Salbutamol Sulphate," 1480–1483 (James E.F. Reynolds et al. eds., The Pharmaceutical Press, 29th ed. 1989).
Mattila, J. et al., Modification by Betamethasone of the Effects of Bronchodilator Drugs on Cholinergic Bronconstriction in Rats, Br. J. Pharmacol., 83(3):607–14 (1984).
Meltzer, E. et al., Comparison of 3 Combinations of Albuterol (A), Theophylline (T), and Beclomethasone (B) in Children with Asthma, J. Allergy Clin. Immunol. 85 (1, Pt. 2):199 (1990) (Abstract).
Miller, R. et al., The Effect of Cytochrome P–450 Induction on Arachidonic Acid Metabolism by Rabbit Lung Microsomal Fractions, Am. Rev. Respir. Dis., 4(2):139 (1989) (Abstract A611).
Molema, J. et al., Effects of Inhaled Beclomethasone Dipropionate on $Beta_2$–Receptor Function in the Airways and Adrenal Responsiveness in Bronchial Asthma, European Journal of Clinical Pharmacology, 34(6):577–83 (1988) (Abstract).
Mora, P. et al., Effect of Regular Inhalation of Combination Inhaler of Beclomethasone Dipropionate and Salbutamol or Bronchial Hyperreactivity in Asthmatic Children, Eur. Resp. J., 1(Supp. 1):15S (1988) (Abstract).
Moscato, G. et al., Salbumatol Plus Beclomethasone Inhibits Early and Late Asthmatic Reactions to Toluenediisocyanate (TDI) Whereas Salbutamol Alone Inhibits Neither, Eur. Resp. J., 2(Supp. 5):398S (1989) (Abstract).
Nathan, R., A Study of Once Versus Twice–Daily Intranasal Fluticasone Propionate in the Treatment of Seasonal Allergic Rhinitis, Journal of Allergy and Clinical Immunology, 85(1, Pt. 2):163 (1990) (Abstract 79).
New Drugs for Tumor Therapy, Asthma and Migraine, Therapiewochi Schweiz., 6:757 (1990).
Nisar, M., et al., Assessment of Reversibility of Airway Obstruction in Patients with Chronic Obstructive Airways Disease, Thorax, 45(3):190–94 (Abstract).
Paggiaro, P. et al. Salbutamol Plus Beclomethasone Inhibits Allergen Induced Early and Late Asthmatic Responses, Whereas Salbutamol Alone Inhibits Neither, Am. Rev. Respir. Dis., 139(4 Pt. 2):A611 (1989) (Abstract).
Palmer, J., The Clinical Development of Salmeterol, Australian and New Zealand Journal of Medicine, 20(3 Supp. 1):521 (1990) (Abstract).
Palmer, J.B.D. et al., $\beta_2$–agonists in asthma, Letters to the Editor, The Lancet, 337:43 (1991).
Pansegrouw, D. et al., The Treatment of Acute Resistant Asthma with a Combination of Beclomethasone and Fenoterol Inhalations, Am. Rev. Resp. Dis., 4(Pt.2):139, A432 (1989).
Pauwels, R. et al., Duration of the Protective Effect of Salmeterol on Methacholine Challenge in Asthmatics, European Respiratory Journal, 3(Supp. 10):225s (1990).
Pesce, L., et al., Steroid–Induced Sensitization of $Beta_2$–Receptors in Chronic Bronchitis, Am. Rev. Resp. Dis., 127(4, Pt. 2):145 (1983) (Abstract).
Phillips, G., Structure–Activity Relationships of Topically Active Steroids: The Selection of Fluticasone Propionate, Respiratory Medicine, 84(Supp. A):19–23 (1990).
Sandstrom, T. et al., A Dose Response Study with a Long Acting Inhaled $\beta_2$–Agonist, American Review of Respiratory Disease, 139(4):Annual Meeting Supplement Abstracts (1989).
Sane, R. et al., Simultaneous Determination of Salbutamol and Beclomethasone Dipropionate from Aerosol Preparations by Reversed–Phase High–Performance Liquid Chromatography, Indian Drugs, 28(2):90–93 (1990).
Slessor, I.M., Becloforte inhaler, British Medical Journal, 286:645 (1983).
Smith, M. et al., Twice Daily Beclomethasone Dipropionate Administered with a Concentrated Aerosol Inhaler: Efficacy and Patient Compliance, Thorax, 41(12):960–63 (1986) (Abstract).
Springer, C. et al., Comparison of Budesonide and Beclomethasone Dipropionate for Treatment of Asthma, Archives of Disease in Childhood, 62(8):815–19 (1987).
Svedmyr, N., The Current Place of $\beta_2$–Agonists in the Management of Asthma, Lung, 168(Supp.):105–110 (1990).
Svendsen, U., Fluticasone Propionate (a New Inhaled Steroid): Clinical Development in Mild to Moderate Adult Asthmatics, European Respiratory Journal, 3(Supp.10):250s, S924 (1990).
Thomas, K. et al., The Effect of Fluticasone Propionate on the Nasal Airway and Cellular Response to Allergen, Clinical and Experimental Allergy, 20(1):20 (1990) (Abstract No. FC57).
Tse, C. et al., Corticosteroid Aerosols in the Treatment of Asthma, The Journal of Human Pharmacology and Drug Therapy, 4(6):334–42 (1984).
Turco, P. et al., Chronic Obstructive Lund Disease: Pathogenic Determinants and Personalized Therapy with Salbutamol Plus Beclomethasone Dipropionate, Clinical Trials Journal, 22(5):381–87 (1985).
Twentyman, O. et al., The Effect of Inhaled Salmeterol on the Allergen–Induced Late Asthmatic Response (LAR) and Increase in Histamine Responsiveness, European Respiratory Journal, 3(Suppl. 10):225s, S794 (1990).
Ullman, A. Inhaled Salmeterol Does Not Cause Tachphylaxis After 14 Days Treatment in Asthmatic Patients, European Respiratory Journal, 2(Supp.8):766 (1989) (Abstract No. 611).
van Schayck, C.P. et al., Increased bronchial hyperresponsiveness after inhaling salbutamol during 1 year is not caused by subsensitization to salbutamol, J. Allergy Clin. Immunol., 86(5):793–797 (1990).
Ventolin compositum, Unlisted Drugs, 33(6):101 (Jun. 1981).

Wallin, A. et al., Formoterol, a New Long Acting $Beta_2$ Agonist for Inhalation Twice Daily, Compared with Salbutamol in the Treatment of Asthma, Thorax, 45(4):259–61 (1990) (Abstract).
Wempe, J. et al., Effect of Bronchodilators on FeV1 and Bronchial Hypperactivity After Pretreatment with Corticosteroids, Am. Rev. Resp. Dis., 139(4, Pt. 2):A435 (1989).
Whelan, C. et al., Salmeterol, But Not Salbutamol, Has Anti–Inflammatory Activity in Guinea–Pig Skin, Br. J. Pharmacol., 97:427P (1989) and Br. J. Pharmacol., 101:528P (1990) (Abstract).

* cited by examiner

MEDICAMENTS

Matter enclosed in heavy brackets [ ] appears in the original patent but forms no part of this reissue specification; matter printed in italics indicates the additions made by reissue.

[This application is a continuation of U.S. patent application Ser. No. 07/578,601, filed Sept. 7, 1990.]

*This application is a continuation of U.S. patent application Ser. No. 07/578,601, filed Sep. 7, 1990, now abandoned.*

This invention relates to improvements in the treatment of asthma and other respiratory disorders. More particularly, it relates to the use of a bronchodilator drug in combination with a steroidal anti-inflammatory drug for the treatment of respiratory disorders such as asthma, and to pharmaceutically compositions containing the two active ingredients.

Asthma is a condition characterized by variable, reversible obstruction of the airways which is caused by a complex inflammatory process within the lungs. In most cases, this process is initiated and maintained by the inhalation of antigens by sensitive atopic individuals (extrinsic asthma). However, in some patients it is caused by other mechanisms which at present are poorly understood but do not involve an allergic process (intrinsic asthma). The disease has therefore two components, spasm of the bronchial (or breathing) tubes and inflammation or swelling of the breathing tubes.

Salbutamon, the first highly selective $\beta_2$-adrenoceptor stimulant has been used successfully and effectively by inhalation for the immediate relief of spasm in asthma. However, when given by inhalation, salbutamol has usually a four to six hour duration of action, which is too short either to control nocturnal asthma or for convenient maintenance of the disease in some patients.

Anti-inflammatory corticosteroids such as, for example, beclomethasone dipropionate have also been administered by inhalation in the treatment of asthma, although unlike salbutamol the therapeutic benefits resulting from reduced inflammation may not be immediately apparent.

It has been recognized that asthma may be treated by using both a bronchodilator or immediate relief and a prophylactic anti-inflammatory corticosteroid to treat the underlying inflammation. Such combination therapy directed at the two main underlying events in the lung (i.e., relief of spasm in the breathing tubes and treatment of inflammation in the breathing tubes) using a combination of salbutamol and beclomethasone dipropionate has previously been proposed (Ventide, Glaxo Group trade mark), but suffers a number of disadvantages in view of the above-mentioned short duration of action exhibited by salbutamol. Thus the need for a 4-hourly dosing regimen may discourage effective patient compliance and also renders the product less than satisfactory in the treatment of nocturnal asthma since the bronchodilator may no remain effective for the duration of the night, leading to impaired sleep for asthmatics troubled by nocturnal cough, breathlessness and wheeze.

The present invention is based on the concept of a novel combination therapy which has markedly greater efficiency and duration of bronchodilator action than previously known combinations and which permits the establishment of a twice daily (bis in dime—b.i.d.) dosing regimen with consequent substantial benefits in, for example, the treatment of asthma, particularly nocturnal asthma.

Thus [we have found] *we believe* that if the $\beta_2$-adrenoreceptor stimulant brochodilator salmeterol and/or a physiologically acceptable salt thereof is combined with the anti-inflammatory corticosteroid fluticasone propionate in a form suitable for administration by inhalation, the resulting compositions may be administered on a b.i.d. basis to provide highly effective treatment and/or prophylactic therapy for asthmatics. In particular *we believe that* such administration [has been shown to] *will* lead to significant improvement in daytime lung functions, requirement for additional symptomatic bronchodilator and almost complete abolition of nocturnal asthma while giving rise to minimal systemic side effects.

Salmeterol is one of a range of bronchodilators having extended duration of action which is described in British Patent Specification No. 2140800, and is systematically named 4-hydroxy-$\alpha^1$-[[[6-(4-phenylbutoxy)hexyl]amino]methyl]-1,3-benzenedimethanol. Fluticasone propionate is one of a range of topical anti-inflammatory corticosteroids with minimal liability to undesired systemic side effects which is described in British Patent Specification No. 2088877, and is systematically named S-fluoromethyl 6α,9α-difluoro-11β-hydroxy-16β-methyl-17α-pripionyloxy-3-oxoandros-1,4-diene-17β-carbothionate. [We have found] *We believe* these two compounds to be particularly compatible and complementary in their activity and thus highly effective in the treatment of asthma and other respiratory disorders.

Thus according to one aspect of the invention there are provided pharmaceutical compositions comprising effective amounts of salmeterol (and/or a physiologically acceptable salt thereof) and fluticasone propionate as a combined preparation for simultaneous, sequential or separate administration by inhalation in the treatment of respiratory disorders.

The invention additionally relates to the use of salmeterol (and/or a physiologically acceptable salt thereof) and fluticasone propionate in the manufacture of pharmaceutical composition as combined preparations for simultaneous, sequential or separate administration of salmeterol and fluticasone propionate by inhalation in the treatment of respiratory element.

According to further feature of the invention there is provided a method of treating respiratory disorders which comprises the simultaneous, sequential or separate administration by inhalation of effective amounts of salmeterol (and/or a physiologically acceptable salt thereof) and fluticasone propionte.

Suitable physiologically acceptable salts of salmeterol include acid addition salts derived from inorganic and organic acids, such as the hydrochloride, hydrobromide, sulphate, phosphonate, maleaste, tartrate, citrate, benzone, 4-methoxybenzoate, 2- or 4-hydroxybenzoate, 4-chlorobenzoate, p-toluenesulphonate, methanesulphonate, ascorbate, salicylate acetate, fumarate, succinate, lactate, glutarate, gluconate, tricarballylate, hydroxynaphthalencarboxylate e.g. 1-hydroxy- or 3-hydroxy-2-naphthalenecarboxylate, or oleate. Salmeterol is preferably used in the form of its 1-hydroxy-2-napthalene carboxylate salt ( hydroxynaphthoate).

For administration by inhalation, the compositions according to the invention are conveniently delivered by conventional means, e.g. in the form of a metered dose inhaler prepared in a conventional manner or in combinations with a spacer device such as the Volumatic (Glaxo Group trade mark) device. In the case of a metered dose inhaler, a metering valve is provided to deliver a metered amount of the composition. Spray compositions may for example be formulated as aqueous solutions or suspensions and may be administered by a nebuliser. Aerosol spray formations, for example in which the active ingredients are suspended, optionally together with one or more stabilisers, in a propellant, e.g. a halogenated hydrocarbon such as trichlorofluoromethane, dichlorofluoromethane, 1,2-dichlorotetrafluoroethane, trichlorotrifluoroethane, monochloropentafluoroethane, chloroform or methylene chloride, may also be employed. The two drugs may be administered separately in similar ways.

Alternatively, for administration by inhalation or insufflation, the compositions according to the invention may take the form of a dry powder composition, for example a powder mix of the active ingredients and a suitable carrier such as lactose. The powder compositions may be presented in unit dosages form in, for example, capsules, cartridges or blister packs from which the powder may be administered with the aid of an inhaler such as the Rotahaler inhaler (Glaxo Group trade mark) or in the case of blister packs by means of the Diskhaler inhaler (Glaxo Group trade mark).

The ratio of salmeterol to fluctuations propionate in the compositions according to the invention is preferably within the range of 4:1 to 1:20. The two drugs may be administered separately in the same ratio. Each metered dose or actuation of the inhaler will generally contain from 25 μg to 100 μg of salmeterol and from 25 μg to 500 μg of fluticasone propionate. As hereinafter indicated, it is intended that the pharmaceutical compositions will be administered twice daily.

A suitable daily dose of salmeterol for inhalation is in the range 50 μg to 200 μg.

A suitable daily dose of fluticasone propionate for inhalation is in the range 50 μg to 2000 μg depending on the severity of the disease.

The precise dose employed will of course depend on the method of administration, the age, weight and condition of the patient and will be determined by the clinician depending on the severity and the type of asthma.

In order that the invention may be more fully understood, the following example are given by way of illustration only.

EXAMPLE 1

Metered Dose Inhaler

| Active Ingredient | Target per Actuation | Per Inhaler % w/w |
|---|---|---|
| Salmeterol (as hydroxynaphthoate) | 25.0 μg | 0.0448 |
| Fluticasone propionate | 25.0 μg | 0.0309 |
| Stabiliser | 5.0 μg | 0.0076 |
| Trichlorofluoromethane | 23.70 mg | 27.8759 |
| Dichlorodifluoromethane | 61.25 mg | 72.0588 |

EXAMPLE 2

Metered Dose Inhaler

| Active Ingredient | Target per Actuation | Per Inhaler % w/w |
|---|---|---|
| Salmeterol (as hydroxynaphthoate) | 25.0 μg | 0.0448 |
| Fluticasone propionate | 50.0 μg | 0.0618 |
| Stabiliser | 7.5 μg | 0.0106 |
| Trichlorofluoromethane | 23.67 mg | 27.8240 |
| Dichlorodifluoromethane | 61.25 mg | 72.0588 |

EXAMPLE 3

Metered Dose Inhaler

| Active Ingredient | Target per Actuation | Per Inhaler % w/w |
|---|---|---|
| Salmeterol (as hydroxynaphthoate) | 25.0 μg | 0.0448 |
| Fluticasone propionate | 250.0 μg | 0.3088 |
| Stabiliser | 25.0 μg | 0.0309 |
| Trichlorofluoromethane | 23.45 mg | 27.5567 |
| Dichlorodifluoromethane | 61.25 mg | 72.0588 |

EXAMPLE 4

Metered Dose Inhaler

| Active Ingredient | Target per Actuation | Per Inhaler % w/w |
|---|---|---|
| Salmeterol (as hydroxynaphthoate) | 25.0 μg | 0.0448 |
| Fluticasone propionate | 125.0 μg | 0.1544 |
| Stabiliser | 15.0 μg | 0.0175 |
| Trichlorofluoromethane | 23.56 mg | 27.7244 |
| Dichlorodifluoromethane | 61.25 mg | 72.0588 |

EXAMPLE 5

Metered Dose Inhaler

| Active Ingredient | Target per Actuation | Per Inhaler % w/w |
|---|---|---|
| Salmeterol (as hydroxynaphthoate) | 100.0 μg | 0.1791 |
| Fluticasone propionate | 250.0 μg | 0.3088 |
| Stabiliser | 25.0 μg | 0.0309 |
| Trichlorofluoromethane | 23.43 mg | 27.4224 |
| Dichlorodifluoromethane | 61.25 mg | 72.0588 |

In Examples 1 to 5 micronised fluticasone propionate and micronised salmeterol (as the hydroxynaphthoate) are added in the proportions given above either dry or after predispersal in a small quantity of stabiliser (disodium dioctylsulphosuccinate, lecithin, oleic acid or sorbitan trioleate)/trichlorofluoromethane solution to a suspension vessel containing the main bulk of the trichlorofluoromethane solution. The resulting suspension is further dispersed by an appropriate mixing system using, for example, a high shear bladder, ultrasonic or a microfluidiser until an ultrafine dispersion is created. The suspension is then continuously recirculated to suitable filling equipment designed for cold fill or pressure filling of dichlorodifluoromethane. Alternatively, the suspension may be prepared in a suitable chilled solution of stabiliser, in trichlorofluoromethane/ dichlorodifluoromethane.

EXAMPLE 6

Metered Dose Dry Powder Formulation

| Active Ingredient | μg/cartridge or blister |
|---|---|
| Salmeterol (as hydroxynaphthoate) | 36.3 |
| Fluticasone propionate | 50.00 |
| Lactose Ph. Eur. | to 12.5 mg or to 25.0 mg |

EXAMPLE 7

Metered Dose Dry Powder Formulation

| Active Ingredient | μg/cartridge or blister |
|---|---|
| Salmeterol (as hydroxynaphthoate) | 72.5 |
| Fluticasone propionate | 50.00 |
| Lactose Ph. Eur. | to 12.5 mg or to 25.0 mg |

EXAMPLE 8

Metered Dose Dry Powder Formulation

| Active Ingredient | μg/cartridge or blister |
|---|---|
| Salmeterol (as hydroxynaphthoate) | 72.5 |
| Fluticasone propionate | 100.00 |
| Lactose Ph. Eur. | to 12.5 mg or to 25.0 mg |

EXAMPLE 9

Metered Dose Dry Powder Formulation

| Active Ingredient | μg/cartridge or blister |
|---|---|
| Salmeterol (as hydroxynaphthoate) | 72.5 |
| Fluticasone propionate | 250 |
| Lactose Ph. Eur. | to 12.5 mg or to 25.0 mg |

EXAMPLE 10

Metered Dose Dry Powder Formulation

| Active Ingredient | μg/cartridge or blister |
|---|---|
| Salmeterol (as hydroxynaphthoate) | 72.5 |
| Fluticasone propionate | 500.0 |
| Lactose Ph. Eur. | to 12.5 mg or to 25.0 mg |

EXAMPLE 11

Metered Dose Dry Powder Formulation

| Active Ingredient | μg/cartridge or blister |
|---|---|
| Salmeterol (as hydroxynaphthoate) | 145.0 |
| Fluticasone propionate | 250.0 |
| Lactose Ph. Eur. | to 12.5 mg or to 25.0 mg |

In Examples 6 to 11 the active ingredients are micronised and bulk blended with the lactose in the proportions given above. The blend is filled into hard gelatin capsules or cartridges or in specifically constructed double foil blister packets (Rotadisks blister packs, Glaxo Group trade mark) to be administered by an inhaler such as the Rotahaler inhaler (Glaxo Group trade mark) or in the case of the blister packs with the Diskhaler inhaler (Glaxo Group trade mark).

I claim:

1. A pharmaceutical composition comprising effective amounts of salmeterol or a physiologically acceptable salt thereof and fluticasone propionate as a combined preparation for simultaneous[, sequential or separate] administration by inhalation in the treatment of respiratory disorders.

2. A composition as claimed in claim 1, wherein salmeterol is present as its 1-hydroxy-2-naphthalenecarboxylate salt.

3. A composition as claimed in claim 1 presented in the form of a metered dose inhaler or a metered dry powder composition.

4. A composition as claimed in claim 1 in dosage unit form containing 25–100 μg of salmeterol or a physiologically acceptable salt thereof and 25–500 μg of fluticasone propionate per dosage unit.

5. A composition as claimed in claim 2 presented in the form of a metered dose inhaler or a metered dry powder composition.

6. A composition as claimed in claim 2 in dosage unit form comprising 25–100 μg of the 1-hydroxy-2-naphthalenecarboxylate salt of salmeterol and 25–500 μg of fluticasone propionate per dosage unit.

7. A composition as claimed in claim 6 presented in the form of a metered dose inhaler or a metered dry powder composition.

[8. The use of salmeterol or a physiologically acceptable salt thereof and fluticasone propionate in the manufacture of pharmaceutical compositions as combined preparations for simultaneous, sequential or separate administration of salmeterol and fluticasone propionate by inhalation in the treatment of respiratory disorders.]

[9. A method of treating respiratory disorders which comprises the simultaneous, sequential or separate administration by inhalation of effective amounts of salmeterol or a physiologically acceptable salt thereof and fluticasone propionate.]

[10. A method as claimed in claim 9 wherein the salmeterol or a physiologically acceptable salt thereof and the fluticasone propionate are administered on a twice daily basis.]

[11. A method as claimed in claim 10 wherein the effective amount of salmeterol or a physiologically acceptable salt thereof 50–200 μg per day and the effective amount of fluticasone propionate is 50–1000 μg per day.]

* * * * *